United States Patent
Morawietz et al.

(10) Patent No.: US 6,218,580 B1
(45) Date of Patent: Apr. 17, 2001

(54) PROCESS FOR INTERMOLECULAR ETHERIFICATION AND ETHER CLEAVAGE

(75) Inventors: Marcus Morawietz, Hanau; Thomas Haas, Frankfurt; Olaf Burkhardt, Alzenau; Rudolf Vanheertum, Kahl, all of (DE)

(73) Assignee: Degussa-Huls Aktiengesellschaft, Frankfurt am Main (DE)

( * ) Notice: Subject to any disclaimer, the term of this patent is extended or adjusted under 35 U.S.C. 154(b) by 0 days.

(21) Appl. No.: 09/186,892

(22) Filed: Nov. 6, 1998

(30) Foreign Application Priority Data

Nov. 7, 1997 (DE) ................................. 197 49 201

(51) Int. Cl.$^7$ ...................................... C07C 43/11
(52) U.S. Cl. ............................ 568/619; 568/618
(58) Field of Search ...................... 568/619, 618

(56) References Cited

U.S. PATENT DOCUMENTS 2,441,597  5/1948  Remensnyder .

FOREIGN PATENT DOCUMENTS

| 43 25 753 | 2/1995 | (DE) . |
| 44 22 051 | 1/1996 | (DE) . |
| 195 10 438 | 9/1996 | (DE) . |
| 0550611B1 | 7/1993 | (EP) . |
| 0492283B1 | 8/1995 | (EP) . |

OTHER PUBLICATIONS

Database WPI Section Ch, Week 8947, Derwent Publications Ltd., AN 89–343233, XP002093255, JP 01 254636, Oct. 11, 1989.

Database WPI, Section Ch, Week 9237, Derwent Publications Ltd. Class A41, AN 92–303557 XP002093256 and JP 04 208242.

C. Montassier, "Polyol Conversion Into Furanic Derivatives on Bimetallic Catalyst, Nature of the Catalytic Sites", Journal Of Molecular Catalysis; Bd. 91, 1994, pp. 119–128, XP002093254.

*Primary Examiner*—Paul J. Killos
(74) *Attorney, Agent, or Firm*—Smith, Gambrell & Russell, LLP

(57) ABSTRACT

The acid-catalyzed intermolecular etherification of mono- or polyhydric alcohols and acid-catalyzed ether cleavage in the presence of water may be improved if etherification or ether cleavage is carried out in the presence of an acid catalyst and, additionally, a hydrogenation catalyst under a hydrogen atmosphere. The process relates in particular to the etherification of diols, triols and tetrols with the formation of hydroxyethers.

18 Claims, No Drawings

PROCESS FOR INTERMOLECULAR ETHERIFICATION AND ETHER CLEAVAGE

INTRODUCTION AND BACKGROUND

The present invention relates to a process for intermolecular etherification of mono- or polyhydric alcohols and for ether cleavage.

In a more particular aspect, the present invention relates to the treatment of the alcohol in the case of etherification or of the ether in the case of ether cleavage in an aqueous phase in the presence of an acid catalyst at a temperature of at least 100° C. Even more particularly, the invention is directed at intermolecular etherification of diols, triols and tetrols with the formation of the corresponding di-, tetra- and hexahydroxyethers.

During the intermolecular etherification of alcohols in the presence of water and an acid catalyst, an equilibrium is established in a known way with the ether formed. Accordingly, ethers can also be formed and cleaved under the same reaction conditions in the process according to the invention. Etherification products of polyhydric alcohols, hereinafter known generally as polyhydroxyethers, are raw materials useful for various fields of application, including for the preparation of polyester resins, lubricants, PVC stabilizers and plasticizers.

Although intermolecular etherification is a basic reaction of organic chemistry, major problems often arise during the etherification of diols, triols, tetrols and other polyols due to insufficient selectivity towards the desired hydroxyether and due to the formation of polymers and colored impurities. In the case of etherification of 1,2-diols, the problem can be solved by using epoxides. In the case of etherification of diols with more than 2 carbon atoms between the hydroxyl groups, such as propane 1,3-diol or butane 1,4-diol for the purpose of obtaining monoetherification products, a hydroxyl function is usually protected before etherification is carried out—see J. Chem. Soc. Perkin Trans 1(1), (1992), 153–156. However, as a result, the etherification process becomes laborious and expensive.

The polyhydroxyethers of the di- and tripentaerythritol type (di- and tripenta) which are becoming increasingly important in industry, and the corresponding polyhydroxyethers of trimethylolethane (TME) and trimethylolpropane (TMP) can be obtained as coupling products in the well known preparation of penta, TME and TMP by way of an aldol and Cannizzaro reaction by varying the reaction parameters. The ether yields are mostly limited and always coupled with the preparation of the principal product penta, TME or TMP; see U.S. Pat. No. 2,441,597 and JP-A-8-176048.

According to JP-A-4-208242, pentaerythritol (penta) can be etherified in the melt in the presence of sulfuric acid with a dipenta selectivity of 35%, based on a penta conversion of 10 to 15%. A similar process for the preparation of dipenta from penta but in which the acid catalyst used is a phosphate of Ti, Al, Cr and Zr is known from EP-B 0 462 283.

Disadvantages of the process carried out in the absence of a solvent are the mostly large proportion of higher etherification products such as tri-, tetra- and polypenta and the formation of intensely colored impurities. A further disadvantage is the use of an organic solvent. As the conversion of penta has to be kept low in order to obtain a high dipenta selectivity, the labor involved in the work-up also increases. The process of the cited EP patent may also be carried out in the presence of water or an aprotic dipolar solvent: the selectivity towards dipenta may reach about 70% and the penta conversion 15% if sulfolane is used as solvent; a disadvantage, however, is the need to use an organic solvent.

About 8% dipenta and 3% tripenta are formed (JP-A 7-76541) by treating penta with urea (8 h, 190° C.). If, in addition, a catalyst based on zirconium, titanium or tin and a dipolar aprotic solvent such as sulfolane are used, the dipenta yield may be increased to 20 to 25% (JP-A 7-258139, JP-A 7-188086 and JP-A 7-165653). Moreover, the etherification reaction mixture contains the catalyst in partially dissolved form, thereby making separation more difficult.

Alternative processes are based on the partial esterification of the hydroxyl functions of polyols, in order to suppress the production of oligomers or polymers in a downstream etherification (EP-B 0 550 611). The disadvantage of these reactions are the mediocre overall yields and the upstream esterification and the ester cleavage required afterwards in order to obtain the polyhydroxyether as a pure product. As a result of ester cleavage, large quantities of the corresponding carboxylic acid salts are obtained, which must be disposed of.

Whereas intramolecular etherification of sugar alcohols under hydrogenating conditions with $H_2$ in the presence of a hydrogenation catalyst is well known (J. Mol. Cat. 91 (1994) 119–128), these conditions were never applied to intermolecular etherification. Moreover, the catalyst useful life proved to be limited and the selectivity mediocre.

An object of the present invention is, therefore, to obtain dialkylethers, di- and polyhydroxyethers by intermolecular etherification from the corresponding monomeric alcohols in good yield, but particularly with high selectivity with respect to the monoethers, and hereby largely to suppress the formation of higher oligomers, polymers, unsaturated by-products and polymeric secondary products thereof, and also discoloration.

SUMMARY OF THE INVENTION

The above and other objects of the invention can be achieved by a process for the intermolecular etherification of mono- or polyhydric alcohols and for ether cleavage, comprising treatment of the alcohol in the case of etherification or of the ether in the case of ether cleavage in aqueous phase in the presence of an acid catalyst at a temperature of at least 100° C. It is a feature of the present invention that the treatment is carried out in the presence of an acid-stable hydrogenation catalyst under a hydrogen atmosphere.

Surprisingly, it was found that by using a combination of an acid catalyst and a hydrogenation catalyst, and by using water as solvent during the etherification of a polyhydric alcohol under an $H_2$ atmosphere, a high selectivity towards monoethers may be obtained. Moreover, practically no higher oligomeric and polymeric compounds are formed and the reaction mixture remains substantially colorless. In this way, bis(hydroxyalkyl)ethers may be obtained from dihydroxyalkanes, bis(dihydroxyalkyl)ethers from trihydroxyalkanes, and bis(trihydroxyalkyl)ethers from tetrahydroxyalkanes. In a similar way to etherification, simple ethers or ethers containing hydroxyl groups may also be cleaved to the alcohol(s) forming the basis of the ether, which process is promoted by a relatively high water content.

DETAILED DESCRIPTION OF INVENTION

The present invention is described in further detail hereinbelow.

Primary or secondary alcohols, preferably primary alcohols with one or more hydroxyl groups, are amenable to the etherification process according to the invention. Similarly, ethers having primary or secondary carbon atoms on the ether oxygen are amenable to the process for ether cleavage. It is important that the alcohol or ether has sufficient solubility in water or aqueous solutions under the reaction conditions. The alcohols and ethers may contain further functional groups, provided these are stable towards hydrolysis and are not hydrogenated under the hydrogenation conditions according to the invention. In particularly preferred embodiment, aliphatic diols, triols and tetrols are fed to etherification. Examples of diols are propane 1,3-diol, butane 1,4-diol, hexane 1,6-diol, neopentylglycol; examples of triols are glycerol, trimethylolethane (TME), trimethylolpropane (TMP), hexane 1,2,6-triol; an example of tetrols is pentaerythritol. Advantageously, oligomeric ethers (ethers with two and particularly more than two ether bridges) are fed to ether cleavage; examples are di-, tri-, tetra- and polypenta, di-, tri-, tetra- and poly-TMP and TME.

Etherification and ether cleavage according to the invention takes place in the presence of water. If necessary, the solution to be etherified may additionally contain, apart from the mono- or polyhydric alcohol and water, other acid-stable and hydrogenation-stable solvents such as an aprotic dipolar solvent; the use of a purely aqueous solution is, however, preferred. Advantageously, the alcohol and the water are used in a weight ratio from 10 to 1 to 1 to 5, preferably from 4 to 1 to 1 to 4, and particularly 3 to 2 to 1 to 2. In the case of ether cleavage, the ether and water are used preferably in a weight ratio from 1 to 4 to 1 to 20, particularly 1 to 6 to 1 to 12.

The reaction takes place at a temperature of at least 100° C., usually at a temperature from 120 to 380° C. A temperature from 120 to 300° C. is preferred, and 200 to 300° C. is particularly preferred.

The presence of an acid catalyst is required for ether formation and ether cleavage. With regard to the Hammet acid definition, reference is made to: Studies in surface science and catalysis, Vol. 51 (1989): *"New solid acid and bases"* by Tanabe et al., page 5. It is possible to use mineral acids such as $H_2SO_4$, HCl and $H_3PO_4$, organic carboxylic and sulfonic acids and acid solid catalysts, of which the $H_0$ value of the Hammet acid function is less than +2, particularly less than −3. Mineral acids are less preferred because they have to be neutralized after the reaction and the salts have to be separated from the reaction mixture and disposed of.

In order to organize the work-up of the reaction mixture of ether formation or ether cleavage as simply as possible, a carboxylic acid whose boiling point is below that of the ether or alcohol to be prepared, particularly a $C_1$ to $C_{12}$-monocarboxylic acid, is used as catalyst according to a preferred embodiment. A carboxylic acid from the series comprising formic acid, acetic acid and propionic acid is particularly preferred. Such carboxylic acids can be separated from the reaction mixture by distillation and then recycled.

The acid solid catalysts with $H_0$ less than +2 are substances from the series comprising: natural and synthetic silicate substances, such as montmorillonite, mordenite and acid zeolites; acids firmly bound to inorganic support materials such as $SiO_2$, $Al_2O_3$ or $TiO_2$, such as, in particular, phosphorus oxides/phosphoric acids; oxides such a gamma-$Al_2O_3$, $TiO_2$, $ZrO_2$, $SnO_2$, $Bi_2O_5$, $Sb_2O_5$, $MoO_3$, $WO_3$; mixed oxides such as $SiO_2$—$Al_2O_3$ or $SiO_2$—$TiO_2$, $Al_2O_3$—ZnO, $SiO_2$—$ZrO_2$, $SiO_2$—$SnO_2$, $SiO_2$—$MoO_3$, $SiO_2$—$WO_3$; heteropolyacids, for example, polytungstosilicates and polytungstophosphates; metal salts such as $AlPO_4$, $FePO_4$, $Zn_3(PO_4)_2$, $Mg_3(PO_4)_2$, $Ti_3(PO_4)_4$, $Zr_3(PO_4)_4$; cation exchange such as exchangers containing sulfonate groups based on polystyrene, polymeric perfluorinated resins or preferably organopolysiloxanes (Deloxan® from Degussa AG). Particularly preferred acid solid catalysts for ether formation and cleavage according to the invention are zeolites of the H-Y, H-beta and H-ZSM 5 type.

The quantity of acid catalysts used which are soluble in the reaction mixture is generally from 0.1 to 20 wt. %, particularly 0.5 to 10 wt. %, in each case based on the mono- or polyhydric alcohol to be converted or on the ether to be cleaved. The quantity of solid acid catalysts used depends both on their activity and the chosen reaction temperature; the quantity used can be determined easily by orientation tests.

The principal feature of the invention is that, in addition to the acid catalyst, a conventional hydrogenation catalyst is present and ether formation/cleavage is carried out in a hydrogen atmosphere. The hydrogen partial pressure is generally from at least 0.1 to 15 MPa, preferably from 1 to 15 MPa, and particularly 3 to 10 MPa.

Although homogeneous and heterogeneous catalysts may be used as hydrogenation catalysts, heterogeneous catalysts are preferred because it is thereby easy to separate the catalyst from the reaction mixture, for example, by filtration. The active component contained in conventional hydrogenation catalysts is a noble metal from the series comprising Ru, Rh, Pd and Pt, or a transition metal from the series Cu, Cr, Co, Ni, Fe, including in particular Raney nickel catalysts and chromite catalysts; bimetal catalysts of a transition metal and noble metal may also be used. The use of a hydrogenation catalyst containing one or more transition metals is advantageous only if the catalyst has sufficient acid stability under the reaction conditions.

Preferred hydrogenation catalysts for the process according to the invention are noble metal catalysts in metallic form, such as so-called blacks of Ru, Rh and particularly Pd and Pt, or in supported form. Suitable support materials for Ru, Rh, Pd and Pt are activated carbon, aluminum oxide, $SiO_2$, $TiO_2$ and other metal oxides and silicates. The quantity of noble metal of supported noble metal catalysts is mostly from 0.0001 to 10 wt. %, in the case of Pd preferably from 0.01 to 1 wt. %, and in the case of Ru preferably from 0.01 to 0.1 wt. %. The optimum quantity of noble metal catalysts used, which depends on the activity of the catalyst, the reaction temperature and the $H_2$ pressure, will be determined by the skilled person by orientation tests. Generally speaking, the quantity used in the case of commercial supported catalysts is from 0.01 to 10 wt. %, particularly 0.01 to 1 wt. %, based on the alcohol to be etherified or the ether to be cleaved. Noble metal catalysts in the form of a black or supported catalyst can easily be recycled, and they have a longer useful life than bimetal catalysts based on a noble metal and a transition metal, of the kind used in the known intramolecular etherification (cyclodehydration) in the absence of an acid catalyst.

The process may be carried out batchwise or continuously. In the case of etherification, the mono- or polyhydric alcohol or the ether and water may be mixed upstream of the reactor or fed in parallel to the reactor. If an acid which is soluble in the reaction mixture is used as catalyst, this is added to the reactant, the water or mixture of the two, or introduced separately into the reactor. The solid hydrogenation catalyst may be used as a suspension catalyst or as a fixed bed. If a solid acid catalyst is used, this may be used in a similar way to the hydrogenation catalyst as a suspension or as a fixed bed. It is also possible to use a catalyst containing both acid and hydrogenation-active functions, for example, a zeolite partially loaded with a noble metal. The optimum reaction time may be determined easily by the skilled person by orientation tests.

The reaction mixture may be worked up in a simple manner after the reaction has ended, or after an equilibrium has been established. This work-up may comprise filtration of a solid acid catalyst and of a heterogeneous hydrogenation catalyst. If a distillable acid catalyst, such as a preferred low carboxylic acid, and a heterogeneous hydrogenation catalyst are used, the work-up comprises filtration of the hydrogenation catalyst and separation of the acid catalyst and water by distillation. The remaining reaction mixture is worked up by distillation and/or extraction and/or by crystallization, preferably by distillation and/or crystallization. The analysis of the composition of the reaction mixture or of individual fractions is carried out by GC or HPLC. Polyols and polyethers are preferably silylated with hexamethyldisilazane/DMF prior to analysis and then analyzed by GC.

Advantages of the etherification process according to the invention compared with known processes are high selectivity towards monoethers, the general absence of polymeric ether alcohols and color-imparting by-products. A further advantage is the simplicity of the process, since no additional process steps are required before and after etherification, and no coupling product is produced. In one of the preferred embodiments—use of carboxylic acids or acid solids as catalyst—no salts need to be removed and disposed of either; moreover, the acid catalysts are just as recyclable as the hydrogenation catalysts.

EXAMPLE 1

Etherification of Propane 1,3-diol 1750 g of propane 1,3-diol, 1750 g of water, 17.5 g of 3% Pd/C and 175 g of propionic acid are introduced into a 5 l autoclave. A 60 bar hydrogen pressure is applied at room temperature and the reaction mixture is then heated to 250° C. The mixture is stirred for one hour at this temperature. After cooling, the autoclave is emptied at 80° C., the catalyst is filtered and a representative sample is taken. The water is removed completely in a rotary evaporator, 1630 g of a colorless liquid are obtained, and the residue is analyzed quantitatively by HPLC. The results are summarized in Table 1.

EXAMPLE 2

Etherification of Trimethylolpropane

The reaction is carried out in a similar manner to the specification described in Example 1, but 1750 g of trimethylolpropane are used instead of 1750 g of propane 1,3-diol. The yield is 1713 g of a colorless liquid. The results are summarized in Table 1.

EXAMPLE 3

Etherification of Glycerol

The reaction is carried out in a similar manner to the specification described in Example 1, but 1750 g of glycerol are used instead of 1750 g of propane 1,3-diol. The yield is 1688 g of a colorless liquid. Three different diglycerol isomers are obtained. The results are summarized in Table 1.

EXAMPLE 4

Etherification of Pentaerythritol 1750 g of pentaerythritol, 1750 g of water, 17.5 g of 3% Pd/C and 175 g of propionic acid are introduced into a 5 l autoclave. A 60 bar hydrogen pressure is applied at room temperature and the reaction mixture is then heated to 250° C. The mixture is stirred for one hour at this temperature. After cooling, the autoclave is emptied at 80° C., heated to dissolve the precipitated penta, the catalyst is filtered and a representative sample is taken. The water is removed completely in a rotary evaporator, 1740 g of a colorless solid are obtained, and the residue is analyzed quantitatively by GC. The results are summarized in Table 1.

EXAMPLE 5

Etherification of Pentaerythritol

Procedure similar to Example 4 except that the reaction was carried out at 280° C. within one hour. 1720 g of a colorless solid are obtained. The results are summarized in Table 1.

EXAMPLE 6

Etherification of Pentaerythritol

Procedure similar to Example 4 except that the reaction was carried out at 290° C. within one hour. 1701 g of a colorless solid are obtained. The results are summarized in Table 1.

EXAMPLE 7

Etherification of Pentaerythritol

Procedure similar to Example 4 except that 20 g of beta zeolite were added instead of propionic acid. The reaction was carried out at 250° C. within one hour. 1735 g of a colorless solid are obtained. The results are summarized in Table 1.

EXAMPLE 8

Etherification of Pentaerythritol

Procedure similar to Example 7 except that the reaction was carried out at 280° C. within one hour. 1681 g of a colorless solid are obtained. The results are summarized in Table 1.

COMPARISON EXAMPLE 1

Etherification of Pentaerythritol Without Reducing Reaction Conditions

Procedure similar to Example 5 except that the reaction is carried out without hydrogenation catalyst and under a nitrogen atmosphere. 1723 g of a brown-colored solid are obtained. The results are summarized in Table 1.

TABLE 1

| Reaction | Yield [g] | Conversion [%] | Yield [g] | Selectivity Product [% based on polyol converted] | Selectivity polymeric products [% based on polyol converted] |
|---|---|---|---|---|---|
| E 1 | 1545 g Propane diol | 11.7 | 45.1 g Di-propane diol | 25.5 | <1 |
| E 2 | 1635 g TMP | 6.6 | 53.1 g Di-TMP | 49.5 | <1 |
| E 3 | 1575 g Glycerol | 10.0 | 52.5 g Di-glycerol | 33.2 | <1 |
| E 4 | 1642 g Penta | 6.3 | 55.3 g Dipenta | 54.8 | <1 |
| E 5 | 1616 g Penta | 7.8 | 64.4 g Dipenta | 51.8 | <1 |
| E 6 | 1554 g Penta | 11.2 | 78.6 g Dipenta | 42.9 | <1 |
| E 7 | 1630 g Penta | 6.9 | 61.6 g Dipenta | 54.5 | <1 |
| E 8 | 1481 g Penta | 15.4 | 104.0 g Dipenta | 41.5 | <1 |
| CE 1 | 1426 g Penta | 18.8 | 41.1 g Dipenta | 13.3 | 3 |

In all the tests, the selectivity of the esterification products is a maximum of 5 to 10% of the theoretical.

COMPARISON EXAMPLE 2

Cleavage of Dipentaerythritol Without Reducing Conditions 200 g of a dipentaerythritol, 2500 g of water and 175 g of propionic acid are introduced into a 5 l autoclave. The reaction mixture is heated to 280° C. The mixture is stirred for 17 hours at this temperature. After cooling, the autoclave is emptied at 80° C., heated to dissolve the precipitated polyols, the catalyst is filtered and a representative sample is taken. The water is removed completely in a rotary evaporator, 155.9 g of an intensively colored solid are obtained and the residue is analyzed quantitatively by GC. The results are summarized in Table 2.

EXAMPLE 10

Cleavage of Dipentaerythritol Under Reducing Conditions

The reaction is carried out in a similar way to Example 9, but before the reaction commences a 60 bar hydrogen pressure is applied and 17.5 g of Pd/C are added. 160.9 g of a colorless solid are obtained and the residue is analyzed quantitatively by GC. The results are summarized in Table 2.

TABLE 2

| Reaction | Yield [g] | Conversion [%] | Yield [g] | Selectivity Product [% based on polyol converted] |
|---|---|---|---|---|
| CE 2 | 76.5 g Dipenta | 61.7 | 19.0 g Penta | 14.4 |
|  |  |  | 0.78 g Tripenta | 0.6 |
| E 10 | 55.8 g Dipenta | 72.1 | 62.1 g Penta | 40.2 |
|  |  |  | 2.7 g Tripenta | 1.9 |

Further various and modifications of the foregoing will be apparent to those skilled in the art and are intended to be encompassed by the claims.

German priority application 197 49 201.0 is relied on and incorporated herein by reference.

We claim:

1. A process for intermolecular etherification of mono- or polyhydric alcohols comprising treating an alcohol in aqueous phase in the presence of an acid-stable hydrogenation catalyst under a hydrogen atmosphere at a temperature of at least 100° C.

2. The process according to claim 1, wherein the alcohol is a polyhydric alcohol.

3. The process according to claim 1, wherein the alcohol is a alcohol selected from the group consisting of diols, triols and tetrols and is etherified in the presence of water with the formation of hydroxyethers.

4. The process according to claim 1 wherein the temperature is from 120 to 380° C. under an $H_2$ partial pressure from 1 to 15 MPa.

5. The process according to claim 2 wherein the temperature is from 120 to 380° C. under an $H_2$ partial pressure from 1 to 15 MPa.

6. The process according to claim 4, wherein the temperature is from 180 to 280° C. and at an $H_2$ pressure from 3 to 10 MPa.

7. The process according to claim 5, wherein the temperature is from 180 to 280° C. and at an $H_2$ pressure from 3 to 10 MPa.

8. The process according to claim 1 wherein the catalyst contains a noble metal selected from the group consisting of ruthenium, rhodium, palladium, platinum and mixtures thereof.

9. The process according to claim 1 wherein the hydrogenation catalyst is used in a quantity from 0.0001 to 10 wt. %, based on the alcohol to be etherified or the ether to be cleaved.

10. The process according to claim 1 wherein the hydrogenation catalyst is used in a quantity from 0.01 to 1 wt. %, based on the alcohol to be etherified or the ether to be cleaved.

11. The process according to claim 1 wherein the acid catalyst used is an aliphatic carboxylic acid with 1 to 12 carbon atoms.

12. The process according to claim 1 wherein said acid is a monocarboxylic acid selected from the group consisting of formic acid, acetic acid and propionic acid.

13. The process according to claim 1 wherein the acid catalyst is used in a quantity from 0.1 to 20 wt. %, in each case based on the polyol.

14. The process according to claim 1 wherein the acid catalyst is used in a quantity from 0.5 to 10 wt. %, in each case based on the polyol.

15. The process according to claim 1 wherein the acid catalyst used is a heterogeneous catalyst selected from the group consisting of acid zeolites, acid metal oxides, phosphates and silicates, and organopolysiloxanes containing sulfonic acid groups.

16. The process according to claim 1 wherein said catalyst contains acid and hydrogenation-active functions based on a zeolite loaded with a noble metal selected from the group consisting of Pd, Pt, Ru and Rh and with an $H_0$ value of less than +2.

17. The according to claim 1 wherein said catalyst contains acid and hydrogenation-active functions based on a zeolite loaded with a noble metal selected from the group consisting of Pd, Pt, Ru and Rh and with an $H_0$ value of less than −3.

18. A process for intermolecular etherification of mono- or polyhydric alcohols to produce a hydroxy ether comprising treating an alcohol selected from the group consisting of a diol, triol and tetrol to carry out an etherification in the presence of an aqueous phase in the presence of an acid-stable hydrogenation catalyst under a hydration atmosphere at a temperature of at least 100° C.

* * * * *